(12) United States Patent
Wagner et al.

(10) Patent No.: US 12,419,998 B2
(45) Date of Patent: Sep. 23, 2025

(54) TUNING ADHESION AT CONTACTING DEVICE INTERFACES: GEOMETRIC TOOLS FOR MINIMIZING SURFACE FOULING

(71) Applicants: UNIVERSITY OF PITTSBURGH-OF THE COMMONWEALTH SYSTEM OF HIGHER EDUCATION, Pittsburgh, PA (US); UPMC, Pittsburgh, PA (US); UNIVERSIDAD DE SANTIAGO DE CHILE, Santiago (CL)

(72) Inventors: William R. Wagner, Gibsonia, PA (US); Sachin Shankar Velankar, Pittsburgh, PA (US); Sang Ho Ye, Pittsburgh, PA (US); Edith Tzeng, Presto, PA (US); Luka Pocivavsek, Pittsburgh, PA (US); Enrique Cerda, Santiago (CL)

(73) Assignees: UNIVERSITY OF PITTSBURGH-OF THE COMMONWEALTH SYSTEM OF HIGHER EDUCATION, Pittsburgh, PA (US); UNIVERSIDAD DE SANTIAGO DE CHILE, Santiago (CL); UPMC, Pittsburgh, PA (US)

( * ) Notice: Subject to any disclaimer, the term of this patent is extended or adjusted under 35 U.S.C. 154(b) by 885 days.

(21) Appl. No.: 16/340,157

(22) PCT Filed: Oct. 18, 2017

(86) PCT No.: PCT/US2017/057111
§ 371 (c)(1),
(2) Date: Apr. 8, 2019

(87) PCT Pub. No.: WO2018/075595
PCT Pub. Date: Apr. 26, 2018

(65) Prior Publication Data
US 2021/0236700 A1    Aug. 5, 2021

Related U.S. Application Data

(60) Provisional application No. 62/409,645, filed on Oct. 18, 2016.

(51) Int. Cl.
*B32B 7/022*    (2019.01)
*A61F 2/06*    (2013.01)
(Continued)

(52) U.S. Cl.
CPC .............. *A61L 33/062* (2013.01); *A61F 2/06* (2013.01); *A61L 27/26* (2013.01); *A61L 29/049* (2013.01);
(Continued)

(58) Field of Classification Search
None
See application file for complete search history.

(56) References Cited

U.S. PATENT DOCUMENTS

| | | |
|---|---|---|
| 2005/0021131 A1 | 1/2005 | Venkatraman et al. |
| 2012/0058302 A1 | 3/2012 | Eggenspieler et al. |

(Continued)

FOREIGN PATENT DOCUMENTS

| | | |
|---|---|---|
| EP | 3470456 A1 | 4/2019 |
| WO | 2013049626 A1 | 4/2013 |

OTHER PUBLICATIONS

Extended European Search Report Issued in EP Patent Application No. 17862979.6, Dated Apr. 7, 2020.

*Primary Examiner* — Christopher T Schatz
(74) *Attorney, Agent, or Firm* — Carol A. Marmo; Eckert Seamans Cherin & Mellott, LLC

(57) ABSTRACT

The present invention relates to substrates and composites having dynamic, reversible micron-level luminal surface
(Continued)

deformation including texture or geometric instabilities, e.g., surface wrinkling and folding. The surface deformation and its reversal to the original surface form or to another, different surface form, is effective to reduce or prevent surface fouling and, more particularly, in certain applications, to reduce or prevent unwanted platelet adhesion and thrombus formation. The substrates and composites include a wide variety of designs and, more particularly, biomedical-related designs, such as, synthetic vascular graft or patch designs.

5 Claims, 1 Drawing Sheet

(51) Int. Cl.
| | |
|---|---|
| A61L 27/26 | (2006.01) |
| A61L 29/04 | (2006.01) |
| A61L 33/06 | (2006.01) |
| B32B 1/08 | (2006.01) |
| B32B 3/28 | (2006.01) |
| B32B 37/10 | (2006.01) |
| B32B 37/16 | (2006.01) |
| B32B 38/00 | (2006.01) |
| B81C 1/00 | (2006.01) |

(52) U.S. Cl.
CPC ............... *B32B 1/08* (2013.01); *B32B 3/28* (2013.01); *B32B 7/022* (2019.01); *B32B 37/1054* (2013.01); *B81C 1/00206* (2013.01); *A61F 2210/0076* (2013.01); *A61F 2240/001* (2013.01); *A61F 2250/0018* (2013.01); *A61L 2430/20* (2013.01); *B32B 37/16* (2013.01); *B32B 2038/0028* (2013.01); *B32B 2309/16* (2013.01); *B32B 2535/00* (2013.01); *B81C 2201/0156* (2013.01); *B81C 2201/0163* (2013.01)

(56) References Cited

U.S. PATENT DOCUMENTS

| | | | |
|---|---|---|---|
| 2012/0212820 A1 | 8/2012 | Jiang et al. | |
| 2014/0017454 A1* | 1/2014 | Boyce | C09D 5/28 |
| | | | 427/535 |
| 2014/0230854 A1* | 8/2014 | Lopez | A61M 25/0017 |
| | | | 15/104.03 |
| 2015/0202065 A1 | 7/2015 | Shalev et al. | |
| 2015/0202821 A1 | 7/2015 | Saha et al. | |

* cited by examiner

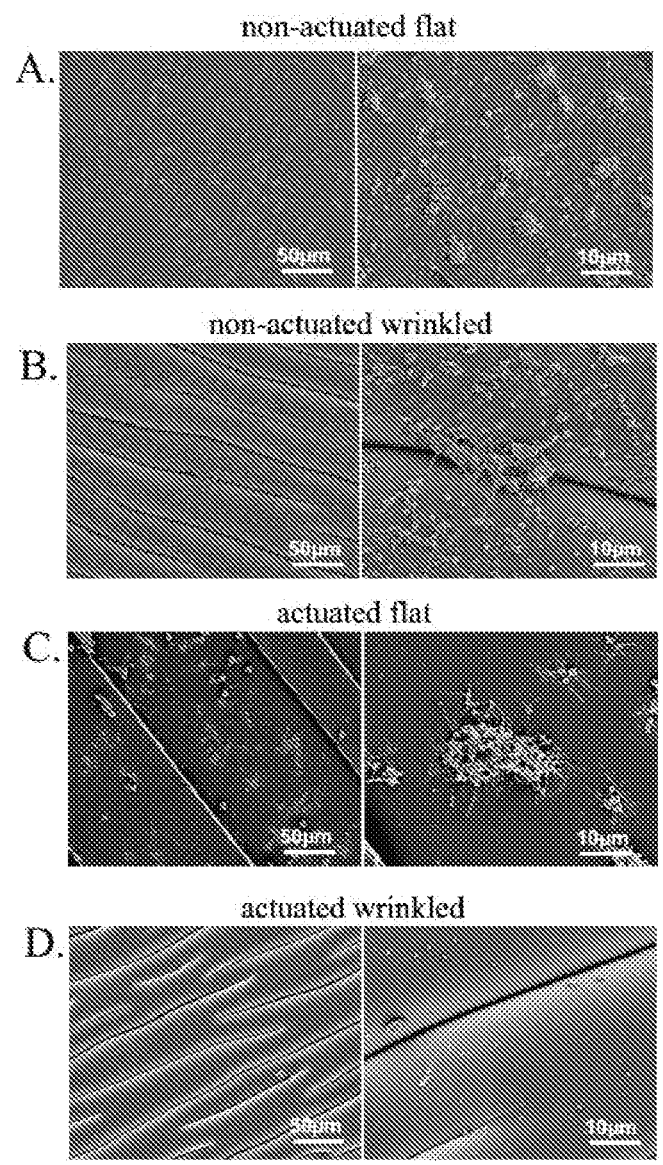

TUNING ADHESION AT CONTACTING DEVICE INTERFACES: GEOMETRIC TOOLS FOR MINIMIZING SURFACE FOULING

CROSS-REFERENCE TO RELATED APPLICATIONS

This application is a U.S. National Stage Application under 35 U.S.C. § 371 of PCT International Application No. PCT/US2017/057111, entitled "TUNING ADHESION AT CONTACTING DEVICE INTERFACES: GEOMETRIC TOOLS FOR MINIMIZING SURFACE FOULING," filed on Oct. 18, 2017, which claims priority under 35 U.S.C. § 119(e) from U.S. provisional patent application No. 62/409,645, entitled "TUNING ADHESION AT CONTACTING DEVICE INTERFACES: GEOMETRIC TOOLS FOR MINIMIZING SURFACE FOULING," filed on Oct. 18, 2016, the contents of which are incorporated herein by reference.

FIELD OF THE INVENTION

The present invention relates to substrates and composites having dynamic, reversible surface deformation including texture or geometric instabilities, e.g., surface wrinkling and folding. The surface deformation and its reversal to the original surface form or to another, different surface form, e.g., from an initial topography to a different topography, is effective to reduce or prevent surface fouling in medical or industrial applications and, more particularly, in certain applications, to reduce or prevent unwanted platelet adhesion and thrombus formation. The substrates and composites include a wide variety of designs and, more particularly, biomedical-related designs, such as, synthetic vascular graft, vascular shunt, patch designs, or other surfaces that contact blood. Similar principles can be used to design surfaces that avoid foulants encountered in other applications including bacterial or algal fouling, fouling by marine organisms, fouling in the petrochemical industry, ice formation on surfaces, mineral deposition on surfaces.

BACKGROUND OF THE INVENTION

Antifouling activity of surfaces has a wide variety of applications including, but not limited to, blood biofouling. Cardiovascular disease remains the leading cause of morbidity and mortality in the western world with ever-expanding patient populations as the epidemic of diabetes and obesity continues its evolution. For more than forty years, cardiac and vascular surgeons have recognized the need of developing durable, low cost, and efficacious synthetic vascular grafts as alternatives to native artery or vein conduits. While successfully implemented in large diameter aortic surgery, the use of polyester (Dacron), polyethylene and polytetrafluoroethylene (PTFE) grafts has had more limited success in coronary (CABG), peripheral vascular (PV) and hemodialysis (HD) access surgeries. Existing synthetic grafts have continually shown poor long-term patency in small caliber bypasses (CABG), complex non-laminar flow systems (PV, especially below knee re-vascularization and HD), and bypasses under dynamic external mechanical stress fields from either beating of the heart or graft stretching and bending due to limb movement. Graft failure is linked to intimal hyperplasia and thrombosis, processes that are accelerated in prosthetic grafts largely by platelet activation and adhesion. Controlling platelet biology is a mainstay of clinical practice in cardiovascular disease through the use of medications, such as, aspirin and clopidogrel. A key strategy in new generation synthetic graft design is the chemical modification of luminal graft surfaces with anti-platelet drugs, heparin, and other polymers, such as, phosphatidyl choline mimics with some promising clinical and pre-clinical outcomes.

Natural surfaces, such as the inner lining of arteries, are far superior at resisting unwanted fouling as compared to artificial surfaces. Much of the anti-fouling ability is attributable to the non-thrombogenic surface provided by the endothelial cells that line the internal surface of the entire circulatory system. Synthetic surfaces fare poorly in blood contact and generally foul rapidly due to platelet adhesion and thrombus formation. There has been an enormous effort in the medical community to create synthetic surfaces that resist fouling for use in catheters, dialysis devices, and vascular implants such as heart valves, and prosthetic blood vessels. Material scientists have addressed the problem of fouling through chemical surface modification to reduce interfacial energy, however, these strategies are not sufficiently general to create a sustainably non-fouling surface. The various strategies that have been employed for improving hemocompatibility include fluorination of surfaces, bonding heparin to the surface, and polyethylene glycol modification. The resulting surfaces can be used for long term blood contact, e.g. for heart valves or vascular grafts. Nevertheless, for vascular conduits, clinical studies have shown that such surface modifications have had limited long-term benefit in improving graft patency. In general, synthetic grafts, typically made of PTFE or polyester, perform poorly in bypasses to blood vessels below the knee. In such surgeries, autologous (i.e. the patient's own) veins are the preferred conduit with higher rates of patency. A disadvantage of these vein conduits is the morbidity associated with the additional surgery needed to harvest the vein.

Many current approaches for improving hemocompatibility of synthetic surfaces are "chemical" in nature and involve the modification of the chemical composition of the blood contact surface, e.g. fluorination reduces surface adhesion strength, polyethylene glycol provides a highly hydrated surface, and heparin bonding activates antithrombin. The present invention relates to a very different approach of antifouling activity of surfaces induced by topographic changes of the blood-contacting surface.

Nature solves the problem of surface self-renewal by using a multi-scale approach. Inherently, "living" and molecular aspects of natural surfaces include a biochemical powerhouse of specialized interfacial cells, such as the endothelium lining of blood vessels or epithelial cells on skin and hollow viscus organs. On a more macroscopic level, many natural surfaces are endowed with non-flat surface morphology or topography. Many conduits in the body (arteries, esophagus, small intestine) are heavily corrugated or wrinkled. Arteries, in particular, exhibit wrinkles that can fully or partially flatten out as the arteries dilate or distend in response to blood pressure changes during the cardiac cycle. Wrinkling, a continuous and smooth surface amplitude undulation is one of the most ubiquitous topographic patterns observed in nature: arteries, lung surfactant, ureter, skin, mussel byssus, intestines, and the brain. Many of these wrinkling interfaces are also under constant threat of biofouling such as platelet/thrombus adhesion in arteries or bacteria in the lung/ureter/skin and on marine surfaces. Furthermore, these natural surface topographies often change or at function of driving forces in the environment, such as, the wrinkling and un-wrinkling of arteries with pulse pressure.

The present invention relates to dynamic surface topography that can improve antifouling characteristics and functionality, and a new mechanism of antifouling. In certain embodiments, topographic actuation from a smooth to a wrinkled surface induces a decrease in foulant attaching to the surface. The surface remains undamaged during the process and hence, repeated actuation yields a "self-renewing" surface that can resist biofouling.

An object of the present invention is to provide the ability of surface actuation, or cyclical wrinkling and unwrinkling, to reduce platelet adhesion and aggregation regardless of the chemical make-up of the surface. It is contemplated and understood that similar concepts may be applied to blood biofouling, but more specifically, to provide new kinds of vascular grafts that rely on continuous topographic actuation to stay clean, e.g., free of biofouling. Another object of the present invention is to provide synthetic surfaces that resist biofouling by demonstrating mechanisms and properties inherent to natural surfaces, e.g., artery surfaces. The surfaces transition from wrinkled to smooth when strained. For example, surfaces can wrinkle when compressed and become smooth when stretched.

In general, it is desired to design and develop a new approach to the problem of vascular graft failure due to undesirable cell adhesion. The addition of surface geometric instabilities in terms of wrinkling and folding to mimic native arterial luminal geometry may provide a coarse-grained biophysical control parameter for platelet surface aggregation and adhesion. This strategy and mechanism may be applied to a wide variety of existing graft materials in open and endovascular devices, providing a cost-effective and implementable modification to current standards of healthcare. Moreover, the new designs may be used on any blood contacting catheter, such as, a venous central line, infusion port, Hickmann line, and tunneled dialysis catheter (TDC). These lines, especially the longer indwelling ones, have a high risk of thrombosis and failure. Formulating a catheter with an external or internal surface that wrinkles and un-wrinkles is a matter of adding an additional layer to existing catheters. Furthermore, while for the implanted vascular graft or endograft the wrinkling and un-wrinkling would be driven by pulse pressure, an external catheter may be connected with a small drive mechanism to simplify the design. These applications are discussed in more detail herein for ease of description. However, it is contemplated and understood that an object of the invention is to employ the inventive concepts in a wide variety of applications.

SUMMARY OF THE INVENTION

In one aspect, the invention provides a composite that includes a first layer composed of a first material; a second layer composed of a second material; a ratio of modulus of the first layer to the second layer from about 3:1 to about 10,000,000:1; an initial base topography exhibited by the first layer, and a subsequent different topography exhibited by the first layer, wherein the first layer transitions from the initial base topography to the subsequent different topography as a result of strain applied to the composite.

The first material can be selected from the group consisting of metal, ceramic, plastic, elastomer, crosslinked polymer, and mixtures and blends thereof. In certain embodiments, the first material is selected from the group consisting of polyester, polyolefin, polyethylene, polypropylene, polytetrafluoroethylene, polyethylene terephthalate, polydimethylsiloxane, epoxy, crosslinked polyester, cyanoacrylate, and mixtures and blends thereof.

The second material can be selected from the group consisting of natural rubber, synthetic rubber, fluoroelastomer, silicone rubber, silicone gel, thermoplastic polyurethane elastomer, thermoplastic polyolefin elastomer, thermoplastic vulcanisate, acrylic elastomer, and mixtures and blends thereof.

The different topography may be selected from the group consisting of wrinkles, folds, dimples, protuberances, and combinations thereof.

The composite can have a configuration selected from the group consisting of a monolayer, bilayer or multilayer. The composite can have a configuration in which one or more of the layers of the monolayer, bilayer or multilayer is/are not continuous. The composite can be in tubular or shell forms.

In another aspect, the invention provides a method of actuating a surface to transition between a base topography and a different topography. The method includes (a) forming a composite, which includes obtaining a material; modifying all or a portion of the material such that a ratio of modulus of a modified portion to an unmodified portion is from about 3:1 to about 10,000,000:1, or a ratio of modulus of an unmodified portion to a modified portion is from about 3:1 to about 10,000,000:1, or (b) forming a composite, which includes selecting a first layer composed of a first material; selecting a second layer composed of a second material, wherein a ratio of modulus of the first layer and the second layer is from about 3:1 to about 10,000,000:1; and connecting the second layer to the first layer; applying a strain to the composite; and transitioning the modified or unmodified material in step (a) or the first layer in step (b) from the base topography to the different topography.

The transitioning can be effective for anti fouling. Additionally, the transitioning can effective for controlling adhesion.

The transitioning may include activating the topography, producing instability of the topography, controlling wavelength of the topography, and reverting to base surface or deforming to another different topography.

The strain can be determined by equation (1):

$$\epsilon^h = f(P, E, L_1, L_2, \ldots) \tag{1}$$

wherein, $\epsilon_h$ is strain, P is pressure, E is modulus, $L_1$, $L_2$ are the relevant geometric parameters of the system.

The optimizing the transitioning from the base topography to the different topography can be according to equation (2):

$$g(\mathcal{K}) = 1 - f(\mathcal{K}) = 1 - \mathcal{K}_c / \Delta \mathcal{K} \sim 1 - (l_{ec} \Delta \mathcal{K})^{-1} \tag{2}$$

wherein, $\mathcal{K}$ is the curvature, $\Delta \mathcal{K}$ is the change in curvature, is $\mathcal{K}_c$ the critical curvature, and $g(\mathcal{K})$ is the degree of surface renewal.

BRIEF DESCRIPTION OF THE DRAWINGS

A further understanding of the invention can be gained from the following description of the preferred embodiments when read in conjunction with the accompanying drawing in which:

FIG. 1 shows scanning electron microscope images of platelet deposition on interface surfaces of composites, in accordance with certain embodiments of the invention.

DETAILED DESCRIPTION OF THE PREFERRED EMBODIMENTS

The present invention relates to substrates and composites having dynamic, reversible surface deformation including texture or geometric instabilities, e.g., surface wrinkling and folding. The surface deformation and its reversal to the original surface form or to another, different surface form, is effective to reduce or prevent surface fouling and, more particularly, in certain applications, to reduce or prevent unwanted platelet adhesion and thrombus formation. The substrates and composites include a wide variety of designs and, more particularly, biomedical-related designs, such as, synthetic vascular graft or patch designs.

Furthermore, the present invention relates to novel, self-cleaning, anti-thrombotic synthetic surfaces. The inner surfaces of arteries and veins are naturally anti-thrombogenic, whereas synthetic materials placed in contact with blood quickly foul with thrombus. The synthetic surfaces according to the present invention use actuating surface topography to reduce or preclude thrombus fouling. The synthetic surfaces are constructed to repeatedly transition between original and different topographies, e.g., smooth and wrinkled states.

When placed in contact with blood, for example, these synthetic surfaces display significantly less platelet deposition and thrombosis as compared e same materials exposed to blood under static conditions, e.g., absent of topography transitioning.

The invention provides a novel mechanism of antifouling in which topographic actuation and the ability to cycle from a smooth to a wrinkled surface, and to another different surface, induces de-lamination of films/fouling adhered to the surface. The surface remains undamaged during the entire process and hence, repeated actuation and reversibility yields a "self-renewing" surface that can resist biofouling.

Wrinkling, a continuous and smooth surface amplitude undulation, is one of the most ubiquitous topographic patterns observed in nature: arteries, lung surfactant, ureter, skin (e.g., human, dolphin and mussel byssus), intestines, and the brain. Many of these wrinkling interfaces are also under constant threat of biofouling, such as, platelet/thrombus adhesion in arteries or bacteria in the lung/ureter/skin and on marine surfaces. Surface wrinkles, in accordance with the invention, can be generated using a laminar composite, wherein two layers are mismatched in thickness and stiffness.

The novel synthetic substrates in accordance with the invention can be used for a wide variety of applications and, more particularly, for biomedical applications, such as, for vascular grafts and patches. In certain embodiments, the synthetic vascular grafts and patches can be used to replace or repair native artery and vein conduits. In other embodiments, the synthetic substrate designs can be used as new catheter designs. The synthetic substrate designs can include various shapes and sizes, such as, but not limited to, cylindrical, tubular and shell forms. In certain embodiments, wherein the vascular grafts and patches are used to mimic a native vein or artery conduit, they may be in the shape of a cylinder or tube. Typically, the inner surface of the cylinder or tube is exposed to blood, which has the potential for fouling of the inner surface. Alternatively, the outer surface may also be exposed to blood or other liquids that have a potential for fouling. Thus, the inner and/or outer surface of the vascular grafts and patches can be deformed, e.g., wrinkled and subsequently smoothed, in accordance with the designs and methods of the invention to reduce or prevent fouling.

In certain embodiments, e.g., for the specific application of prosthetic vascular grafts, pulse pressure, i.e., the continual variation of blood pressure between systole and diastole, may be used to produce topographic actuation. Soft cylindrical tubes are constructed with a luminal, synthetic surface that can transition between smooth and wrinkled states. Upon exposure to blood under continual pressure pulsation, these cylindrical tubes also exhibit significantly less fouling as compared to the same materials exposed to blood under static conditions. The anti-thrombotic activity can be exhibited even when the wrinkles have wavelength of several ten microns, significantly larger than individual platelets. The anti-thrombotic action may be attributable to a novel biofilm delamination process.

For ease of description, the disclosure herein is primarily directed to the deformation of substrates and composites for vascular grafts and patches. However, it is contemplated and understood that the designs and methods of the invention have a wide variety of applications for deformable surfaces in contact with liquids that have potential for fouling the surface and wherein, there is a desire to reduce or prevent fouling of the surface by causing dynamic, reversible deformation of the surface. This includes foulants that may be encountered outside of the medical arena, e.g. biofouling of marine surfaces, mineral depositions in industrial applications, or ice deposition onto surfaces.

In general, the novel synthetic grafts and patches include the use of mechanical energy focused at a liquid/solid interface of a surface. Typically, the surface of the substrate is exposed to a liquid, such as blood, that has a potential for unwanted fouling of the surface. Dynamic, reversible surface texture, e.g., surface wrinkling and/or folding, is used to reduce or prevent unwanted fouling, such as, platelet adhesion and thrombus formation. Known, conventional strategies focus on controlling adhesion via chemical means. The present invention provides surface renewal that can be effective to control fouling. Surface renewal can be the sole mechanism for controlling fouling or may be coupled with known chemical modification approaches.

Dynamic, reversible surface topography can produce an anti-fouling, synthetic surface. For example, activation of surface deformation provides a deformed surface that is not static. The deformed surface can be reversed back to the original surface or the deformed surface can be further deformed to another, different deformation. Thus, the surface can cycle between various geometrical topographies. Without intending to be bound by any particular theory, it is believed that activation of the one or more deformations and the cyclability between the deformations, is effective to reduce or prevent fouling of the surface. Further, it is believed that controlling the deformations and cycling of the deformations can be effective to control or tune the fouling of the surface for use in a variety of applications. For example, in certain embodiments, the present invention is effective to reduce or prevent platelet adhesion from whole blood to a synthetic polymer surface. As a result of surface deformation, platelet adhesion to the surface may be reduced by almost 97%, as compared to platelet adhesion to the surface absent of the surface deformation.

In certain embodiments, a composite may be constructed according to the invention that includes a first layer composed of a first material and a second layer composed of a second material. The first material can be selected from metal, ceramic, plastic, elastomer, crosslinked polymer, and mixtures and blends thereof. Non-limiting examples of the first material for use in the invention can be selected from polyester, polyolefin, polyethylene, polypropylene, polytetrafluoroethylene, polyethylene terephthalate, polydimethylsiloxane (PDMS), epoxy, crosslinked polyester, cyanoacrylate, silicone, and mixtures and blends thereof. A wide variety of suitable polymers are known in the art. The polymer may be selected from those that are known for use in biomedical applications. In certain embodiments, a synthetic polymer surface is composed of PDMS. The second material can be selected from natural rubber, synthetic rubber, fluoroelastomer, silicone rubber, silicone gel, thermoplastic polyurethane elastomer, thermoplastic polyolefin elastomer, thermoplastic vulcanisate, acrylic elastomer, and mixtures and blends thereof.

Endowing the surface of a first layer, e.g., polymeric substrate, with a deformation, e.g., texture, pattern, wrinkles, folds, dimples, protuberances and combinations thereof, can be effective in reducing biofouling by decreasing adhesion of unwanted material, e.g., platelets for vascular grafts, to the surface of the substrate. Surface topography is used to control adhesion, as well as to control wettability, friction, and viscous drag of a surface. Generally, when rough surfaces are prepared from compliant materials, their topography can be changed in response to mechanical, chemical, thermal, or flow fields. Such dynamic surface topography can greatly improve antifouling characteristics/functionality.

A natural arterial luminal surface is not flat, and contains topography that is sensitive to internal pressure. Without intending to be bound by any particular theory, it is believed that surface topographic instabilities, such as, sinusoidal wrinkling and folding, can function as a coarse-grained biomechanical control parameter for platelet surface aggregation and adhesion. A flat surface can result in platelet adhesion thereto, whereas, a surface with wrinkling and folding can prevent unwanted platelet adhesion and thrombus formation. Wrinkles can be generated using, for example, a bilayer composite having a superficial layer bonded to a bulk support layer, wherein the superficial layer is thinner and stiffer as compared to the support layer, and the support layer is softer as compared to the superficial layer.

In certain embodiments, surface wrinkles or folds or dimples or protuberances or combinations thereof, are generated by creating a stiffness mismatch within a multilayer, e.g., bilayer, composite. Different layers of the composite may be composed of silicone rubber or silica or some other combination of materials, of which at least one is stiff and one is soft. One layer is a thin stiff membrane, which is adhered to a different layer that is significantly softer. The soft layer may be denoted as the base layer. In certain embodiments, the stiff layer is in the form of a film, e.g., a polymeric film, which is stiffer, as compared to the stiffness of the lower layer. The stiffness mismatch between the top layer and the bottom layer may be created using various processes. A silicone rubber surface can be stiffened by exposure to ultra-violet ozynolysis (UVO), which vitrifies the surface into a thin layer of silica. The advantage of UVO treatment methods is the ability to create very thin and well-bonded surface layers. To create uniform surface layers with minimal defects, the samples can be positioned in an oxygen-enriched reaction chamber and irradiated for a period of time, such as but not limited to, about 90 minutes. If the irradiation is done to a silicone rubber that is held stretched, then after completing irradiation, releasing the stretch induces the stiff layer to wrinkle, whereas re-stretching would induce a smooth surface. If the irradiation is done to a silicone rubber that is held in its stress-free state, then after completing the irradiation, compressing the silicone rubber induces wrinkles, whereas releasing the compression would induce a smooth surface.

In other embodiments, surface wrinkles or folds or dimples or protuberances or combinations thereof, are generated by bonding a thin stiff film to the surface of a softer sheet of another materials. The stiff material may be polymeric, paper, metallic, ceramic, or other like material, whereas the softer material may be polymeric, rubbery, a polymer foam or a non-polymer foam, or other soft material. If the softer sheet is held prestretched during the bonding process, the surface wrinkles upon releasing the prestretch. If the softer sheet is held relaxed during the bonding process, the surface will wrinkles upon compression.

In still other embodiments, surface wrinkles or folds or dimples or protuberances or combinations thereof, are generated by depositing a thin liquid film onto the surface of a soft material, and then allowing the thin film to change into a stiff solid layer by means of a physical change (e.g. freezing or vitrification) or a chemical change (e.g. chemical reaction, crosslinking, polymerization). If the softer sheet is held prestretched during the bonding process, the solidified surface layer wrinkles upon releasing the prestretch. If the softer sheet is held relaxed during the bonding process, the surface wrinkles upon compression.

In accordance with the invention, a composite can have a configuration selected from a monolayer, bilayer or multilayer. In certain embodiments, one or more of the layers in the configuration is/are not continuous.

In certain embodiments, the multilayer composite includes an elastomeric sheet that is approximately planar, but capable of transitioning from being wrinkled to being smooth when stretched. The elastomeric sheet endowed with a wrinkled surface is bonded to a pneumatic actuator base which is pressurized or strained, causing the sheet to balloon outwards. The stretching of the sheet then causes the wrinkles to smooth. With repeated pressurization and depressurization cycles, the surface is transitioned continually between wrinkled and smooth textures. The wrinkled surface itself is generated using UV-ozone (UVO) treatment of polydimethylsiloxane (PDMS) silicone rubber. The inflation is used to drive a wrinkle-smooth transition at the surface. A pneumatic actuator base cast from silicone is constructed and a sheet of PDMS is bonded to it. The exposed surface of the elastomer sheet is then subjected to UVO treatment, which is known to vitrify the surface into a ~100 nm thin layer of silica which is much stiffer than the elastomer. The wrinkles are generated by irradiating under pressurized conditions when the elastomeric film is distended. Due to the rectangular geometry of the ballooning sheet, the elastomer stretching is predominantly uniaxial, and a stretching of 30% along the short axis is used. The silica layer formed due to UVO treatment is strain free under pressurized conditions but upon reducing the pressure, the elastomer retracts and compresses the silica layer, leading to wrinkling of that layer with a uniform wavelength.

Repeated stretching of a smooth surface, by itself, can reduce blood fouling of the surfaces. Furthermore, continually actuating a surface to transition between a base topography and a different topography further reduces thrombus formation. It is known that the pulsatile flow of the natural circulatory system offers a driving force to provide continual actuation of grafts. Natural arteries expand and contract several percent with every pulse cycle. The normal pressure pulsations can drive small amplitude stretching and relaxation of the synthetic grafts, which can then drive the continual smooth to wrinkled transition of the luminal surface. This concept is illustrated and mimicked by the synthetic substrates and surfaces of the present invention. For example, a cylindrical tube endowed with a stiff inner wall is wrinkled in a low pressure state and smooth when inflated to a higher pressure state.

In general, the invention includes actuating a surface to transition between a base topography and a different topography, wherein a material can be at least partially modified. For example, the material surface can be fully or partially modified. The ratio of modulus of the modified portion to the unmodified portion can be from about 3:1 to about 10,000,000:1, or from about 3:1 to about 1,000,000:1, or from about 3:1 to about 100,000:1; or the ratio of modulus of the unmodified portion to the modified portion can be from about 10,000,000:1 to about 3:1, or from about 1,000,000:1 to about 3:1 or from about 100,000:1 to about 3:1. In certain embodiments, for a composite, the first layer is composed of a first material and a second layer is composed of a second material selected such that the ratio of modulus of the first layer to the second layer is from about 3:1 to about 10,000,000:1, or from about 3:1 to about 1,000,000:1, or from about 3:1 to about 100,000:1. The first layer exhibits an initial or base topography and subsequently exhibits a different topography. The transition from the initial or base topography to the different topography can result from the application of strain to the composite. The strain can be determined by $\epsilon_h = f(P, E, L_1, L_2, \ldots)$, wherein, $\epsilon_h$ is strain, P is pressure, E is modulus, $L_1$, $L_2$ are the relevant geometric parameters of the system.

Laminar composites, wherein two layers are mismatched in thickness and stiffness, are inherently challenging to construct because of the length scale separations and surface concentrated deformations that make de-adhesion a problem. Relevant system parameters include: (i) wrinkle wavelength $\lambda = tY^{1/3}$, where $t$ is membrane thickness and Y is the ratio of membrane to substrate elastic moduli; (ii) wrinkle amplitude $A = \epsilon_{1/2} \lambda$, where $\epsilon$ is surface compressive strain; and (iii) critical surface compressive strain needed for wrinkle onset $\epsilon_w = 1/Y_{2/3}$.

In certain embodiments, synthetic graft designs according to the invention are employed to replace native veins or arteries, wherein cardiac pulse pressure drives or activates the dynamic wrinkling and un-wrinkling of the surface. The cylinder strain under appropriate boundary conditions as a function of internal pressurization up to 8 kPa (pulse pressure) is considered. A hoop strain provides an approximation to this parameter and is a function of cylinder thickness (h), radius (a), modulus $\epsilon$, and pressure (P): $\epsilon_h = (P \times a)/(E \times h)$. The system control parameters, $\lambda$, Y, A, $\epsilon_w$, $\epsilon_h$ are selected and optimized, such that pulsatile flow with a pressure variation in the range of 8 kPa can drive surface wrinkling and un-wrinkling of the inner surface of a cylindrical geometry.

The formula governing wrinkle appearance is generally as follows. A bilayer, with a thin stiff membrane adhered to a soft substrate under an applied strain E, wrinkles with two characteristic length scales: wavelength $\lambda \sim (B/E_s)^{1/3}$ and amplitude $A \sim \lambda E^{1/2}$, where B is the membrane bending stiffness and $E_s$ the substrate modulus. To the flat or weakly wrinkled bilayer is adhered a softer patch of material, e.g. a bacterial film or platelet aggregate forming the nidus of a blood clot on an arterial surface. The interfacial stability is initially dominated by the chemical interaction between the surface and the patch, defined through the adhesion energy V. As the bilayer begins to wrinkle, the topography, characterized by surface curvature $\kappa = A/\lambda^2$ grows as amplitude increases with bilayer compression. At some critical amplitude $A_c$, the adhered patch begins to delaminate from the wrinkled surface forming discrete blisters of length l and amplitude $A_l$ that co-exist with still attached material. Moreover, once de-adhesion nucleates, interfacial cracks spread beyond the initial failure zone inducing delamination of the entire patch. Since the wrinkling mechanics of the bilayer are preserved during this de-adhesion process, the surface may be stretched back to its original clean state, hence the term 'a mechanically-renewing' surface.

There is an interplay between the surface defined topography length scale ($\lambda$) and the patch thickness h (its dominant length scale in plane strain conditions). For thin patches, both $\lambda$ and h play a role in defining interfacial stability. However, as patch thickness increases, delamination becomes independent of patch geometry and is a function of surface topography. The cross-over occurs for $\lambda/h \sim 1$.

A difference between the bio-inspired surface renewal mechanism of the present invention and buckle and wrinkle-delamination mechanisms seen in traditional composite materials, is the de-coupling between the adhered patch elasticity and the mechanics giving rise to surface wrinkling. The wrinkles (topography) participate only in so far as they impose a boundary condition onto the adhered patch. Likewise, the softness of the patch prevents it from influencing the wrinkling mechanism. This allows the wrinkled surface to be renewed but remain mechanically intact, in contrast to buckle-delamination, wherein interfacial failure leads to the suppression of surface wrinkling and overall mechanical failure of the bilayer material.

The present invention may include one or more of the following inventive concepts and benefits, as compared to traditional mechanisms. While the description is directed to antifouling due to competition between elastic energy and adhesion energy, it is contemplated and understood that other mechanisms may also be relevant.

1. A surface renewal mechanism whereby energy release of stored elastic energy in an adlayer drives interfacial crack propagation and therefore, adlayer de-adhesion and surface renewal.

1a. Topography imposes a boundary condition onto the adlayer patch, causing an increase in its elastic energy. The topography and mechanics of the topographic surface are not affected by the adlayer, and participate only through the application of surface-derived boundary conditions, i.e. the topographic surface remains mechanically and chemically intact between actuation cycles. The energy balance calculation leads to a general formal predicting the onset of surface renewal:

$$K_C \sim \frac{1}{\ell_{ec}} \quad (1)$$

Formula 1 defines in the most general way the mechanism. It can be specifically defined for different surfaces and adlayers. $\kappa_c$ is the local curvature of the actuating surface. It is a function both of surface spatial parameters and time: $\kappa_c = \kappa_c(x,y,z,t)$, and $l_{ec}$ is an effective elasto-capillary or elasto-adhesive length scale which combines the elastic properties of the adlayer and the adhesion strength with the substrate.

1.1 Surface Topography-Defining $\kappa_c$

Topography of a general surface is linked to the variation in height along the surface. Geometrically, surfaces can be defined as functions of internal lengths like arc length (l) that move along with the surface or paramerizations in given coordinate systems. A common method is to define a particular height function h(x,y) which is a parameterization of the (x,y)-plane:

$$\vec{r}(l) = x(l)\vec{e}_x + y(l)\vec{e}_y \quad (2)$$

where $\vec{e}_x$, $\vec{e}_y$, and $\vec{e}_z$ are the unit vectors in the x, y, and s directions respectively. The surface curvature is defined as the derivative of the surface tangent vector or second derivative of the spatial functions:

$$\vec{\kappa} = \frac{d\vec{t}}{dl} = \ddot{x}(l)\vec{e}_x + \ddot{y}(l)\vec{e}_y \tag{3}$$

An important realization about these geometric definitions is that they are local and make no assumption on the global geometric or topographic structure of the surface. Furthermore, the above equations do not require that the surface have global continuity. The sole requirement is that there be piecewise continuity that allows a local curvature to be defined. If the functional form of the surface is defined, then a functional form of curvature can be obtained. However, curvature is convenient because it can also locally be linked to well-measured surface length scales. For instance, for a sinusoidally wrinkled surface (which is detailed separately below), the local curvature is $\kappa \sim A/\lambda_2$, where A is wrinkle amplitude and $\lambda$ is the wavelength. Since it is a local parameter, measurement of curvature is not limited to globally well-behaved functions. There are alternative modes of generating surface curvature with a pattern of alternating surface stripes and troughs. In this patterned surface, effective amplitude (individual blade height h) stays relatively constant while the inter-blade separation acts as an effective surface wavelength $\lambda^*$. The curvature in this case is defined as $\kappa_l \sim h/(\lambda^*)^2$.

Depending on the particular mechanics of the surface, either amplitude (local vertical height) or wavelength (local horizontal spacing) or both change during an actuation cycle. The particular initial topography and subsequent loading mechanism will make the surface either a amplitude-driven, e.g., wrinkled surfaces, or wavelength-driven, e.g., striped surfaces, system as it concerns curvature actuation.

From a surface design standpoint, $\kappa_c$ is the target in the fabrication process of the surface, e.g. vascular graft, membrane filter. It is a geometric property of the surface which provides a novel surface tuning parameter not explored previously.

1.2 Adlayer Elasticity and a Surface Adhesion—Defining $l_{ec}$

The surface imposes a deformation field onto the adhered adlayer. The deformation field is a function of surface curvature $\kappa$. The adlayer is removed from the surface once a critical curvature is reached, mainly once the potential elastic energy stored in the adlayer, because of surface curvature, reaches a critical value. The critical value is proportional to or greater than the adhesion strength of the adlayer and surface. It can generally be shown using an energy balance approach between surface and elastic energies that the critical curvature ($\kappa_c$) is proportional to the inverse of an effective elasto-adhesive or elasto-capillary length scale ($l_{ec}$):

$\kappa_c \sim 1/l_{ec}$.

1b. Actuation of surface topography between state 1 and state 2, state of lower and higher curvatures (as defined above), causes the build-up of said elastic energy leading to a critical point occurring at some curvature between state 1 and state 2, at which enough stored energy is accumulated to compete with surface adhesion strength and the onset interfacial failure occurs. Patch de-adhesion and interfacial fracture between patch and surface is driven by release of the stored elastic energy imposed by surface curvature.

The surface is designed with a given initial surface topography, characterized by a curvature $\kappa_i$, and a targeted final surface curvature $\kappa_f$. Built within the design of the surface is a method of changing the surface curvature as a function of some externally or internally imposed boundary conditions by compressing, stretching, or twisting the surface; there may be four canonical loading mechanisms for a cylindrical graft like geometry.

1c. At any given time point, a topographically actuating surface is covered with patches having different structures and geometries, such that $l_{ec}$ is a random variable that can assume the values $0 < l < \infty$ with a distribution P(l). In this framework, the characteristic length is $$\ell_{ec} = <\ell> = \int_0^\infty \ell P(\ell) d\ell.$$

Given a range of $\Delta\kappa$ imposed during each actuation cycle, the fraction of patches meeting detachment criteria $$\kappa\ell = 1) \text{ is } \int_{R_f}^{R_i} P(\ell) d\ell$$

where the limits of integration represent the radii of curvature for the final ($R_f = 1/\kappa_f$) and initial ($R_i = 1/\kappa_i$) states of the surface. Assuming that actuation begins with a flat surface, $R_i = \infty$, since all patches with $l \geq R_f$ must detach, the fraction of remaining attached patches after a cycle of actuation is:

$$f(\kappa) = 1 \int_{R_f}^\infty P(\ell) d\ell \tag{4}$$

Thus, the surface density of remaining patches (p) is calculated knowing the initial density ($\rho_0$): $\rho = f(\kappa)\rho_0$. To fix ideas, an exponential distribution $$P(\ell) = \frac{1}{\ell_{ec}} e^{\ell/\ell_{ec}},$$

is used, although the results are equally applicable to other distributions. When $K_f l_{ec} >> 1$, it means the imposed curvature is sufficient to detach patches with length scales covering the average and larger lengths, the fraction is $f(\kappa) \approx 1/(\kappa_f l_{ec})$. Defining the critical curvature $\kappa_c = 1/l_{ec}$ for the average value of the critical length and using $\Delta\kappa = K_f$ or this specific case, there is written $f(\kappa) = \kappa_c/\Delta\kappa$. This analysis predicts that for randomly aggregating surface adlayers, surface renewal is improved by increasing the range of surface curvatures $\Delta\kappa$ during each actuation cycle.

The key result of the above analysis is the relation:

$$g(\kappa) = 1 - f(\kappa) = 1 - \kappa_c/\Delta\kappa \sim 1 - (l_{ec}\Delta\kappa)^{-1} \tag{5}$$

It predicts that the degree of surface renewal $g(\kappa)$ is proportional to the ratio of the mean critical curvature or adlayer elasto-capillary length and the range of curvatures during on actuation cycle. Optimized surface renewal is achieved as $g(\kappa)$ approaches 1.

2. Wrinkles impose one specific form of reversible surface topography that can be used to drive surface renewal.

Surface wrinkles are a general and well controlled method of generating reversible surface topography with curvature proportional to a ratio of wrinkle amplitude and wavelength: $\kappa = A/\lambda^2$. Wrinkles are generated by placing a composite (two-layer) surface with a thin stiff layer adhered to a softer thicker layer under a compressive or tensile stress. The wrinkle wavelength ($\lambda$) is a strain free intrinsic length scale which appears after an initial critical compressive strain is achieved ($\epsilon_w = (2E_m/E_s)^{2/3}$). The wavelength is a function of the thickness of the stiffer thinner layer (h) and the ratio of the elastic moduli of the two layers:

$$\lambda = 2^{1/3} \pi h \left(\frac{E_m}{E_s}\right)^{1/3} \quad (6)$$

where $E_m > E_s$. Wrinkle amplitude is a function of in-plane nominal strain ($\epsilon_n$) beyond $\epsilon_w$ and $\lambda$:

$$A = \pi_1 \epsilon_n^{1/2} \lambda \quad (7)$$

The dynamic surface curvature can be written using geometric definitions and the above relations as $$\kappa(\epsilon_n) = \left\{ 2^{1/3} \pi^2 \left(\frac{E_s}{E_m}\right)^{1/3} \left(\frac{1}{h}\right) \right\} \cdot \epsilon_n^{1/2} = A \cdot \epsilon_n^{1/2} \quad (8)$$

Equation 8 shows that for a wrinkling surface the degree of surface curvature is proportional to an intrinsic constant of the material construction $\mathcal{A}$ (function within curly brackets of Equation 8) and imposed nominal compressive strain. When being used to design materials with actuating surface curvatures, the designer sets $\mathcal{A}$ through the choice of materials for the given application and tunes it given the known amount of available strain in the given system. Within the formalism defined in 1 above, the criterion for surface renewal for wrinkled surfaces can be re-written specifically for wrinkled surfaces as:

$$\kappa_{cw} = \kappa(\epsilon_n) = A \cdot \epsilon_n^{1/2} \sim \frac{1}{\ell_{ec}} \quad (9)$$

Given that in most real-life settings the relevant and controllable parameter during surface operation will be imposed nominal strain, a critical nominal strain can be defined:

$$\epsilon_{nc} \sim \frac{1}{(A\ell_{ec})^2} \quad (10)$$

2a. For wrinkled surfaces, the precise relationship between critical surface curvature $\kappa_c^{t<\lambda}$, adhesion strength $\gamma$, adlayer strength E, and adlayer thickness t in the THIN adlayer regime (meaning adlayer thickness t less than wrinkle wavelength $\lambda$) is given by:

$$\kappa_c^{t<\lambda} = \frac{A_c}{\lambda^2} \approx \frac{\gamma^{1/2}}{E^{1/2} t^{3/2}} \quad (11)$$

The critical nominal strain for surface renewal can therefore be written as:

$$\epsilon_{nc}^{t<\lambda} \sim \frac{\gamma}{A^2 E t^3} \quad (12)$$

This relation is validated through computer simulations.

As the surface wrinkles, the topography imposes a boundary condition onto the patch, causing an increase in its elastic energy. Assuming the deformation occurs quasi-statically, in the thin patch limit, bending energy dominates patch elasticity and is estimated as $$U_B \sim \int_A B\kappa^2 dA \approx B\left(\frac{A}{\lambda^2}\right)^2 wL,$$

where L is system length, w its width, and $B = Et^3/12(1-\nu^2)$ is patch bending stiffness. As part of the patch (length l<L) de-adheres, the elastic energy gains two new contributions: the new bending energy of the detached region with smaller curvature $$U_B' \sim B\left(\frac{A_l}{l^2}\right)^2 wt$$

and the elastic energy dissipated during the transition:

$$U_B'' \sim B\left(\frac{A}{\lambda^2}\right)^2 wt.$$

Since new surfaces are created during interfacial failure, the interfacial energy $U_A = \int_A \gamma dA$, must be added to the elastic term, giving the total energy:

$$U_T \sim U_B + \left(B\left(\frac{A_F}{l^2}\right)^2 - B\left(\frac{A}{\lambda^2}\right)^2 + \gamma\right) wl,$$

where A=wl is the area of detached interface. Using the inequality $A_l/l^2 \ll A/\lambda^2$, which by the inextensibility condition $A_l/l = A/\lambda \approx p\sqrt{\epsilon}$, is equivalent to assuming $l \gg \lambda$, allows us to neglect the second term in $U_T$, and obtain the condition for patch de-adhesion by minimizing the reduced total energy with respect to l: $\delta_l U_T = 0$, giving the critical amplitude for patch de-adhesion as $$A_c \sim \left(\frac{\gamma}{B}\right)^{1/2} \lambda^2 \approx \left(\frac{\gamma}{E}\right)^{1/2} \frac{\lambda^2}{t^{3/2}} = \left(\frac{\lambda^2}{E^{1/2} t^{3/2}}\right) \gamma^{1/2}.$$

The critical simulation amplitudes are normalized by $\lambda^2/(E^{1/2} t^{3/2})$.

2b. For wrinkled surfaces, the precise relationship between critical surface, curvature $\kappa_c^{t>\lambda}$, adhesion strength $\gamma$, adlayer strength E, and adlayer thickness t in the THICK adlayer regime (meaning adlayer thickness t greater than wrinkle wavelength) is given by:

$$\kappa_c^{t>\lambda} = \left(\frac{\gamma}{E}\right)^{1/2} \frac{1}{\lambda^{3/2}} \quad (13)$$

The critical nominal strain for surface renewal therefore can be written as $$\epsilon_{nc}^{t>\lambda} \sim \frac{\gamma}{A^2 E \lambda^3} \quad (14)$$

This relation is validated through computer simulations as well as experiments.

In the limit $t/\lambda > 1$, the increased thickness of the patch prevents energy release by pure rotation or bending. The simulations and experiments point toward a near-interface mechanism whereby only the strains near the bound interface are released. The elastic strain energy of a thick free slab is $$U_0 = \frac{1}{2} E \epsilon^2 L w t$$

where $\epsilon$ is the strain imposed and Lwt is the volume. However, near the wrinkled interface, the local strain energy is increased because of the extra surface deformation field proportional to $\epsilon_f \sim \delta_y u_x \sim A/\lambda$. Similarly, the layer deformed by the wrinkled substrate has a volume Lwd where d is a penetration length estimated as $d \sim \lambda$. Hence, the strain energy in the attached thick patch is $$U_S \approx U_0 + \frac{1}{2} E \epsilon_f^2 L w \lambda.$$

Since the patch is thick, once a subset of length l detaches, it initially lacks sufficient freedom to bend and release the compressive strain by rotating, therefore it keeps its initial strain energy $U_0$. The new elastic energy is $$U_E^t \approx U_0 - \frac{1}{2} E \epsilon_f^2 l w \lambda,$$

where the last term gives the release of elastic energy because of fracture. Including the interfacial energy as above, gives the total elastic energy for $$t/\lambda > 1 : U_T^t \sim U_0 + \frac{1}{2} E \epsilon_f^2 (L - l) w \lambda + \gamma w l.$$

Minimizing $U_T^t$ with respect to l yields the critical amplitude in the thick patch limit:

$$A_c^t \sim \left(\frac{\gamma}{E}\right)^{1/2} \lambda^{1/2}.$$

2c. Silicone composite materials (a softer silicone substrate with a stiffer silicone skin) both in flat and cylindrical geometries with wrinkles in the 30 to 1000 μm range, with an inner diameter of 3 mm and wall thickness of 1 mm were constructed, and shown to have decreased platelet adhesion. For both the flat and cylindrical systems, the wrinkle wavelength is selected as outlined above, Equation 6. The surface curvature is actuated between zero and a maximum curvature following the scaling outlined in Equation 8. In all of the validation experiments, the cylinders were designed such that maximum curvature $\kappa_{max}$ achieved during an actuation cycle was larger than the critical curvature needed to dislodge adhered platelets or micro-thrombi formed on the surface: $\kappa_{max} > \kappa_c^{<\lambda}$ (2a) and $\kappa_{max} > \kappa_c^{t>\lambda}$ (2b).

The present invention relates to developing a vascular graft with internal wrinkling topography that is actuated with pulse pressure. Biomedical and non-biomedical applications are encompassed. Moreover, various geometries and loading conditions can be considered, for example, as described below.

Biomedical Applications

Biofouling in biomedical devices is essentially either in the form of blood surface fouling or bacterial adhesion. Topographic actuation can dramatically impact blood fouling and in particular platelet adhesion. The following is a list of target applications and devices.

Blood Fouling
Vascular Graft

Cylindrical vascular grafts are target applications. Internal surface topographic actuation is driven by internal pressure actuation. Methods of assembly include a key step of creating a strain mismatch between the thin internal membrane and thicker substrate. This can be accomplished using a planar pre-stretch system or via an alternative method where by the polymers are cast onto acrylic rods of varying sizes and membranes are mismatched to achieve the desired pre-strains. The internal diameters can vary and, in certain embodiments, can be ~3 mm, which serves an un-met clinical need where current small caliber (<6 mm) grafts have prohibitively high failure/thrombosis rates. Target applications include below knee lower extremity bypass and coronary bypass (CABG) operations, hemodialysis grafts, as well as venous reconstruction. Different vascular beds experience different flow and hemodynamic forces (coronaries, tibias, arterial versus venous), the graft design can be targeted for optimal topographic actuation given particular vascular bed or patient input parameters such as flow rate, diastolic, systolic, and mean pressures.

Vascular Patch

Patches with wrinkles can be assembled using a similar set of techniques as for the cylinders. Planar patch wrinkling and wrinkle actuation is produced using an oscillating pressure field. This geometry can be extended to allow for dual surface wrinkling of the patch. Standard one surface wrinkling can be utilized in patch angioplasty arterial reconstructions to again prevent surface fouling from platelet adhesion, artificial heart membranes such as in the Carmat heart, and venous reconstructions. Dual surface wrinkling can be utilized in patch closure/reconstruction of ventricular defects where there is blood contact on both sides of the membrane. Lastly, dual wrinkle patches can be used in path angioplasty arterial reconstruction in potentially infected surgical beds as can often be encountered in the groin during femoral exploration.

Dual Surface Graft

A dual surface graft can undergo topographic actuation w wrinkl g on both the external and internal cylinder surfaces. Such graft constructions can be used in infected or possibly contaminated vascular fields to prevent luminal platelet adhesion and external surface graft colonization by bacteria. Applications include surgical oncology venous reconstructions where external contamination is a risk because of concurrent GI track surgery. This construction could also be used in central line constructions (TDC, port).

Endografts

Stent supported grafts are subject to the same degree (if not greater) of blood fouling and thrombosis as surgically implanted bypasses. The technology of dynamic topography can be extended to the endograft membrane material. Consideration of the effect of the supporting metal stent structure can be taken into account. The applications are particularly strong in iliac limb thrombosis during endovascular aortic repair (EVAR) and covered small diameter stents (e.g. Viabahn) for lower extremity procedures and potentially in coronary stents.

Hollow Fiber Systems—Dialysis

Continuous renal replacement therapy (CRRT) and hemodyalysis (HD) systems are under constant threat of filter thrombosis. The vast majority of these filters are constructed as modules of hollow fibers, with blood entering the fiber lumen and dialysate fluid around the fibers; exchange of dissolved ions and water occurs across the membranes. In the case of HD, flow rates are high because patients usually have an established high flow AV-fistula or graft; the HD system can also be heparinized. However in CRRT, which is used in acutely ill patients who develop renal failure in an intense care setting, flow rates are often sluggish given only venous access furthermore these patients at baseline have a pro-coagulant state because of the acute pro-inflammatory state they are often in. CRRT circuit failure secondary to thrombosis is very common and a source of sever cost and risk to the patient. Internal and external membrane wrinkling can be conceptualized in hollow fiber arrays, wherein external wrinkling is under axial loading. Modular design of hollow fibers which undergo topographic actuation could substantially decease circuit failure secondary to surface induced thrombosis, especially in CRRT.

External Ventricular Drainage Tubing—EDV

Patients who suffer traumatic brain injury often have a subarachnoid bleed, blood must be drained from the CNS ventricles using a plastic tube. These tubes are under constant threat of fouling and thrombus formation on the inner surfaces which obstructs the therapeutic drainage. Dual tube actuation or only internal actuation can be used.

Bacterial/Non-Blood Fouling

Foley Catheter

Urinary drainage catheters are at constant risk for bacterial surface contamination, surface actuation both externally and internally can be used to prevent bacterial film growth on both surfaces.

Artificial Ureter

Currently no synthetic material is available for ureter reconstructions

Biliary Stents

Biliary stents (often covered like endovascular stent grafts are placed in in the biliary drainage system and under constant threat of surface fouling from adhesion of bile slats and bacteria.

INDUSTRIAL APPLICATIONS

Membrane Filtration

The present invention may have a significant impact on MBR (membrane bio-reactor/waste water ultra-filtration). MBR utilizes hollow fibers (typical dimensions 1.5 mm ID, 2-3 mm OD) made from PVDF or cross-linked polysulfone (possibly other materials) sealed at one end and attached to a vacuum at the other end. The MBR fibers are immersed as a bundle into waste water sludge (very high particulate density), the luminal vacuum draws water across the membrane separating particulates from water. A substantial existing challenge with this filtration technology is fouling on the external fiber surface. This challenge is currently addressed by air scouring the hollow fibers. Driving pressurized air though the fiber bundles mechanically vibrates the fibers and induces disruption of fouling layers deposited on the external surface. There is a need for better anti-fouling methodologies in MBR systems, since air scouring has significant energy costs associated with it, accounting for nearly 40% of operation costs. Dynamic topography provides a potential implementation of fiber external surface topography driven by air scouring, at potentially reduced frequencies, as a method to introduce surface energy to compete with adhesion on a smaller and more targeted length scale. Currently these fibers are on the order of 2m in length. Given the length and thickness (~0.5-1.5 mm) and large stiffness of the current materials, it is unlikely that the fibers bend into modes with curvatures greater than $1$ $m^{-1}$. The dynamic topography approach can increase these surface curvatures by more than 3 orders of magnitude if a targeted surface wavelength of 100-500 microns is achieved. An approach can include using the available surface strain generated by air scouring the entree fiber to driver surface instabilities like wrinkling. The challenge is material selection and the creation of a hollow fiber with a bilayer construction, with a stiffer thinner external layer and a softer thicker inner layer. A similar approach may be applied to other industrial tubing surfaces, such as, but not limited to biopharma reactor chambers and food conduction tubing, such as, in the milk industry.

Ship/Marine Vessel Anti-Fouling

Shear flow over a surface n generate an in-plane displacement on a bilayer surface and lead to reversible surface wrinkling that could drive surface renewal. A two coat paint application can be used having a first coat thicker and softer, and a second much thinner, stiffer layer.

Power Line Anti-Icing

Ice formation on cables is a significant problem for power outages during winter. A strategy for ice disruption is external surface wrinkling and un-wrinkling with the strain being provided by the bending/twisting of the power line by its interaction with the wind.

Directional Wetting/Water Collection

A surface can be wrinkled overnight allowing water condensation onto it and water retention because of the topography. At some other time point (e.g., morning), the surface can be un-wrinkled by application of a simple stretch smoothing out the topography and allowing the water to be collected.

Conduction Tubing

A variety of industrial applications and systems utilize polymer-based tubing to carry complex fluids which often stick to the surfaces of the tubing causing fouling. Examples of this include food processing (milk, dairy, fruit juice, and the like), automotive (file injector systems), non-automotive engines (again fuel injector systems especially in diesel based engines), petrochemical processing (heat exchangers).

Loading Mechanism and Load Mechanics

The standard formulation to generate wrinkles is a compressive in-plane strain onto a bilayer composite structure. Once this strain reaches a critical value proportional to $E_c \sim (2Y)^{-2/3}$, where Y again is the modulus mismatch ratio of the two composite materials, wrinkles appear throughout the surface on the side of the thinner membrane. The physics of wrinkling are not dependent on the source of compressive strain, meaning they are de-coupled for the most part from loading conditions and boundary conditions. As long as the membrane/substrate interface experiences effective compressive strain, wrinkles will appear. For practical applications, the details of the loading mechanism are paramount, since the loading mechanism produces the actuating field which drives surface amplitude actuation and therefor surface renewal. In the theory of shells, nearly every load can be reduced into radial and axial components; as such for the composite cylinders, any possible load encountered in an application will produce wrinkles. Another canonical load is helical twisting along the long cylinder axis. Likewise in planar geometries, a wrinkled patch can be loaded by pressure on either side causing surface actuation. Lastly, how a given topography actuates with the applied global (nominal) strain depends on the physics of that topography. With wrinkles, amplitude actuation scales as the square root of the nominal strain. In the case of non-wrinkle based topographies, there is no analytic formulation to predict the amplitude of surface curvature actuation with the nominal strain field. In this case, each particular system is evaluated with numerical simulations to gain an understanding of topographic changes with a given applied load cycle.

Materials

Broad material properties that are elastomeric (e.g., polyurethane, polyolefin, silicones), metals, and foams (e.g., metals, plastics, gradient of porosity for hollow fiber). The type of materials that can be used is dependent on the mechanism with which topography is generated. In the case of wrinkling, because it induces high surface strains, the materials must be elastic to at least 10 percent strain.

Fabrication Methods

Two approaches include methods for making patches with one-sided wrinkles and cylinders with one- or two-sided wrinkling.

It will be appreciated by those skilled in the art that changes could be made to the embodiments described above without departing from the broad inventive concept thereof. It is understood, therefore, that this invention is not limited to the particular embodiments disclosed, and described in the following examples, but it is intended to cover modifications that are within the spirit and scope of the invention.

EXAMPLES

Example 1

The concept that surface strain and topographic actuation reduce unwanted surface adhesion was tested as follows. This example considered surfaces that were approximately planar, but capable of transitioning from being wrinkled to being smooth when stretched.

An elastomeric sheet endowed with a wrinkled surface was bonded to a pneumatic actuator base which was pressurized. The actuator base comprised a block of stiff rubber with long cavity and the elastomeric sheet was bonded on top of this cavity. The cavity was pressurized, causing the sheet to balloon outwards. The stretching of the sheet then smoothed out the wrinkles. With repeated pressurization and depressurization cycles, the surface transitioned continually between wrinkled and smooth textures. The wrinkled surface was itself generated using UV-ozone (UVO) treatment of polydimethylsiloxane (PDMS, Sylgard-184, Dow Corning, Midland, MI) silicone rubber. This inflation was used to drive a wrinkle-smooth transition at the surface. A pneumatic actuator base cast from silicone RTV-4136M was constructed, and a 5 mm thick sheet of Sylgard 184 PDMS rubber was bonded to it. The exposed surface of the Sylgard elastomer sheet was then subjected to UVO treatment, which vitrified the surface into a ~100 nm thin layer of silica which is much stiffer than the elastomer.

Polydimethylsiloxane (PDMS, Sylgard-184, Dow Corning, Midland, MI) was cast into uniform 5 mm thick films using 10% cross-linker, and cured at 100° C. for 48 hours before use. The films were bonded to pre-cast silicone (Silastic M3, Dow Corning, Midland, MI) actuator bases. To generate surface wrinkles, a stiffness mismatch was created between the thin stiffer top layer and softer bulk silicone. PDMS surfaces were stiffened by exposure to UV ozynolysis (UVO), which vitrified the surface into a ~100 nm thin layer of silica. The advantage of the UVO treatment method was the ability to create very thin and well bonded surface layers. To create uniform surface layers with minimal defects, the samples were positioned 2 cm from a UV source in an oxygen enriched reaction chamber of a Novascan PSD Pro 4 UVO cleaner (Novascan Technologies Inc., Ames, IA), and irradiated for 90 minutes. Irradiation for shorter periods of time created thinner silica layers, however, significant surface inhomogeneities also appeared. Flat samples, in which wrinkling was not desired, were irradiated under zero-strain conditions. To generate wrinkles with PDMS, the surface underwent at least 30% compressive strain. The silicone actuator support layer was designed to allow for expansion of the PDMS surface upon pressurization. Irradiation was performed with the PDMS membrane stretched 30% along the short axis. The silica layer formed under these conditions remained strain free in the pressurized bulk PDMS geometry. When the actuator was de-pressurized, the silica layer was compressed and wrinkles were generated. Given the anisotropic strain along the actuator short axis, wrinkling occurred with the wrinkle neutral direction along the actuator long axis. To minimize Y-type defects in wrinkle wavelength, the pressurized samples were slowly de-pressurized over 12 hours. However, even under the most optimal conditions, Y-type defects were difficult to completely avoid in PDMS samples. Samples were stored in air and at room temperature before use in blood experiments. The above procedure generated unidirectional wrinkles with a uniform wavelength of 50 μm.

The blood contact bioreactor was designed to minimize non-PDMS (non-test) surface contact. This was accomplished by machining a polycarbonate chamber that was set onto the silicone/PDMS actuator surface and masked all but the thin rectangular part of the surface which expanded under actuation. The volume of this chamber was 30 ml. Since standard surface/blood testing requires minimization of any blood/air surface area, a second silicone/PDMS actuator was placed on top of the polycarbonate chamber. The three parts were placed under axial compression. Given the compressible nature of the silicone, a good seal was obtained between the polycarbonate and actuators without the need for any additional sealants that may compromise or leak into the reaction chamber. Valves located at the ends of the polycarbonate chamber allowed easy filling of the reaction chamber with blood and purging of all air. This design allowed testing of two surfaces during each of the blood contact experiments. Once the chamber was filled with 30 ml of ovine blood, the actuators were connected to the actuation circuit. The blood was drawn 15 minutes prior to the contact experiments and kept from coagulating by a small amount of citric acid solution. A peristaltic pump (9000 G series, New Era Pump Systems, Inc., Farmingdale, NY) was connected in series to the two actuators. During each half-cycle, the pump moved 4 ml of water from one actuator chamber to the other, pressurizing one chamber and expanding the PDMS membrane while de-pressurizing the other and contracting its PDMS membrane making the surface wrinkle. This counter-pulsation allowed minimization of any hydrostatic pressure build-up in the actual blood chamber. The blood was not placed into the actual flow circuit, since it was separated from the water based circuit by the PDMS test membranes. The actuation frequency was 0.4 Hz/cycle. The entire bio-reactor was placed into a tissue culture incubator at 37° C. and actuation was carried out for 90 minutes or 2100 cycles.

Whole fresh ovine blood was collected by jugular venipuncture and anticoagulated with sodium citrate solution (10 mM/mL). NIH guidelines for the care and use of laboratory animals were observed, and all animal procedures were approved by the Institutional Animal Care and Use Committee (IACUC) at the University of Pittsburgh.

For the static PDMS test samples, the surface thrombotic deposition was assessed by a simple rocking test after being cut and placed a test tube (BD Vacutainer, with no additives). The test tube was filled with 5 mL of ovine blood and gently rocked for 90 minutes at 37° C. on a hematology mixer (Fisher Scientific, Pittsburgh, PA).

At the completion of actuation or incubation for the static samples, the blood was carefully removed and the surfaces washed 10 times with normal saline. The PDMS surfaces were then cut into 1 cm$^2$ samples. For the actuation experiments, samples were taken at least 1 cm away from the short-axis boundaries where substantial bi-axial strain exists. Samples then underwent standard post-processing for LDH and SEM characterization. In detail, the blood contacted PDMS surfaces were rinsed with DPBS (10 times) to remove any non-adherent blood contents. Samples were then immersed in a 2.5% glutaraldehyde solution of DPBS for 2 h at 4° C. to fix the surface adherent platelets and then serially dehydrated with solutions of increasing ethanol content. Each sample surface was observed by scanning electron microscopy (SEM; JSM-6330-F, JEOL USA, Inc., Peabody, MA) after sputter coating with gold/palladium. Deposited platelets on each surface were also quantified by a lactate dehydrogenase (LDH) assay with an LDH Cytotoxicity Detection Kit (Clontech Laboratories, Inc. Mountain View, CA) after the blood contact.

The results of this experiment are as follows. The PDMS surface that had been UVO-treated without prestretching (and hence remained smooth), exhibited significant thrombus formation after exposure to blood under static conditions with a typical platelet deposition density of roughly 7000 platelets/cm$^2$. The PDMS surface that had been UVO-treated with prestretching (and hence wrinkled), demonstrated even greater thrombus formation when exposed to blood under static conditions, with a platelet deposition density of over 10,000 platelets/cm$^2$. When exposed to blood under continual actuation, both smooth and wrinkled surfaces showed dramatically lower platelet deposition: roughly 1100 platelets/cm$^2$ in the case of smooth surface actuation and roughly 250 platelets/cm$^2$. The more precise quantification is as follows: the smooth actuated surface showed 84% lower platelet deposition than the smooth static surface; the wrinkled actuated surface showed 97% lower platelet deposition than the wrinkled static surface, and the wrinkled actuated surface showed 73% lower platelet deposition than the smooth actuated surface. The wrinkled actuated surface was nearly completely devoid of deposited platelets. Scanning electron microscopy images of these findings are shown in FIG. 1. These findings indicate that repeated stretching—by itself—reduces platelet deposition of interface surfaces. The continually actuating surface topography further reduces platelet deposition by several fold.

This purely mechanical strategy demonstrated the ability to prevent unwanted fouling for surfaces in contact with highly complex fluids, such as, blood. It is believed that this decrease in adhesion results from a competition between surface thermodynamic forces, such as, adhesion and surface elasticity. Adhered platelet patches actuated on dynamically wrinkled surfaces de-adhered because energetically the cost of elastic energy from surface-induced bending was too high. Other mechanisms such as effect of the dynamic wrinkles on fluid mechanics near the surface may also play a critical role.

Example 2

Example 1 showed that a surface that continually transitions between a smooth and wrinkled state has anti-fouling activity against a foulant. If cylindrical tubes can be endowed with such actuating topography on their inner surface, they may be useful for various conduit applications such as vascular grafts. The actuation of such cylinders can be conducted by pulsing the internal pressure of the tubes using any suitable power source. For medical applications, the pressure pulsations of the cardiovascular system may themselves be used for this pulsation. Specifically, blood pressure pulsations may be harnessed to drive small amplitude stretching and relaxation of the synthetic grafts, which can then induce continual changes between smooth to wrinkled states at the luminal surface. The concept is illustrated as follows. A cylindrical tube in its unpressurized state is wrinkled on its inner surface. Pressurizing it is expected to smooth out the wrinkles, analogous to smoothening of an accordion when stretched.

Cylindrical tubes (called "grafts") were fabricated and tested for fouling under blood exposure under continual pulsation. The effect of wavelength on the antithrombotic activity was also examined.

The fabrication method for constructing the grafts was as follows. A several-micron thick film of the stiff silicone RTV-4136M was spread onto a flat surface and cured. A thick layer of a much softer silicone (GI-245) was then spread on this first layer and allowed to cure to form a bilayer. Upon releasing from the flat surface, this bilayer was stress-free and therefore, remained flat and had a smooth surface. To create surface wrinkles, this bilayer was bonded to a second layer of GI-245 (which had been cast separately) that was held prestretched 30-40%. Upon releasing the prestretch, the stiff surface film of RTV-4136M developed strong wrinkles whose wavelength could be tuned by varying the film thickness. The layered sheet was then rolled into a cylinder 10 cm in length and 6 mm in diameter (wrinkle-side inside), and the edges of the cylinder were sutured together. The suture line was sealed externally with a thin coat of GI-245 silicone to provide a water tight suture line. A layer of a different silicone, GI-380, was used to make the pressure needed for expansion/contraction comparable to physiological pressures. The selection of geometric parameters (e.g. thicknesses of the various layers, the degree of prestretch, etc.) was guided by FEM simulations incorporating the properties of the materials used to manufacture the graft. Finite element simulations were performed using the commercial software package Abaqus v6.14 (Simulia, Dassault-Systemes, Providence, RI).

The grafts were designed so that the two pressures would be close to typical diastolic and systolic pressures. The compressive strain that induced wrinkling came from both the prestretch, as well as the strain associated with bending a flat sheet into a cylinder shape. Upon completion of fabrication, but before conducting blood flow experiments, the pressure at which wrinkles appear and disappear was determined. Since the resulting tubes were opaque, this validation could not be done by simple visualization or microscopy. To perform this validation, Optical Coherence Tomography (OCT) using a specialized catheter was employed. OCT worked by collecting images along circumferential cross-sections at high frequencies, and had been used to examine the luminal and mural structure of arteries in vivo. With current OCT technology, the lateral spatial resolution was approximately 50-100 µm. For the validation, the silicone graft was sealed at one end, and the other end was connected to a syringe pump. The graft was inflated and deflated at 0.05-0.1 Hz with water using a while measuring pressure. Simultaneously, an OCT catheter was swept through the graft to image the lumen. It was visually observed that the lumen became much less wrinkled as the pressure was raised from 50 mm Hg to 200 mm Hg, which are in the range of diastolic and systolic pressures in humans. These pressures bracketed the pressure range for the blood fouling experiments.

After calibration of each graft, blood tests were conducted using fresh whole blood from a healthy human donor. Static titanium (i.e. unactuated) control samples were tested in a rocking configuration, such that the blood was constantly shaken gently. The actuated samples were tested as follows. Multiple cylinders with three different wavelengths (1000 µm, 250 µm, and 80 µm) were tested. A vascular access catheter was sutured at one end of the graft, whereas the other end was sutured closed. The catheter access line was split to allow a syringe pump and blood pressure analyzer to be connected simultaneously. The entire system was incubated at 37° C. and actuated for 90 minutes. The actuation volume was set so that the desired high a low pressures, identified from the OCT calibration experiments, were reached, At the end of the blood exposure, the cylinders were cut open and an analyzed with an LDH assay.

The results compared the cross-sections under fully-deflated conditions of the four grafts used in blood tests: one graft with a smooth lumen, and three with wrinkles of various wavelengths. An additional cylindrical graft which was smooth on its inner surface was also tested under static conditions as a control sample. The control smooth silicone graft was thrombotic under static conditions. For the grafts undergoing continual actuation between expanded (smooth) and contracted (wrinkled) states, the sample with a 1000 micron wavelength showed 70% lower platelet adhesion than the control sample which was held static. The grafts with smaller wavelengths showed an even sharper decrease in platelet adhesion, with the smallest wavelength exhibiting 88% lower platelet deposition than the static control.

In actuality, the difference between the samples was larger than cited above because of the significant platelet adhesion evident along the suture line. In fact, it is well known that suture lines are a strong nidus for platelet activation/adhesion and thrombus formation. Therefore, the data for the sutured samples was reanalyzed examining only the sutureless hemicylinder. Excluding the effect of sutures, the actuated graft with the smallest wavelength had 50-fold lower fouling than the static control, and 5-fold lower fouling than the actuated graft with the largest wavelength.

Similar experiments were also conducted using grafts with a completely smooth lumen, and these results were similar to the 1000 micron lumen. This suggested that the 1000 micron wavelengths was, from a blood biofouling perspective, equivalent to a flat surface. In summary, these results confirmed that surface actuation between wrinkled and flat surfaces reduced platelet adhesion and fouling, and demonstrated that smaller wavelengths were more effective. The surface chemistry of the cylindrical constructs (bare silicone) was different from the flat sheets used previously (silica-like surface bonded to silicone). This suggested that the anti-thrombotic effect demonstrated was due to topographic actuation and not specific to the surface chemistry.

Example 3

In Example 2, the cylindrical tubes were fabricated by making a flat bilayer with a wrinkled surface, and then rolling it into a cylinder with the wrinkled surface inside. This left a seam along the side of the tube, which in Example 2 was sutured. Example 3 included a process to create seamless tubes with wrinkles on the inner surface which became smooth as the tube was expanded.

The fabrication procedure was as follows. A rod of desired diameter was given a thin coating of silicone rubber, RTV-4136M. The typical coating thickness was about 50 microns although this may be varied. The RTV-4136M was allowed to cure.

Separately, a smaller diameter rod was coated with a softer silicone, GI-245, to a thickness of about 1-1.5 mm although this may be varied. Upon full curing, this coating was removed from the rod to obtain a tube of silicone of inner diameter equal to that of the small rod.

The above larger diameter rod coated with RTV-4136M was then inserted into the GI-245 tube (stretching the tube due to the mismatch in diameter). A suitable adhesive agent was used to ensure a good bond between the RTV-4136M and the GI-245. The resulting bilayer tube was then removed from the larger diameter rod. Upon removal, the diameter of the tubing was reduced (i.e., the tubing of GI-245 nearly recovered its original diameter). This induced the desired internal wrinkles along the length of the tube.

Analogous to Example 2, OCT imaging was used to verify that internally-pressurizing these tubes caused an increase in diameter and a smoothening of the internal wrinkles. A further external coating of a different silicone may be provided by dip-coating to reduce the inflation.

These tubes were then exposed to platelet-rich plasma (expired, donated from the Pittsburgh Blood Bank) using a blood flow circuit as follows. A Harvard Apparatus Pulsatile Blood Pump for Rabbits was used to drive pulsatile flow. This pump is a positive displacement piston pump which can deliver pulsatile flow. The pump was connected to the seamless bilayer tubes with internal wrinkles. The pump delivered fluid into the seamless tubes, and then back into a collection chamber to be recirculated back into the pump. A valve downstream of the bilayer tubes (i.e., before the fluid was deposited into the collection chamber) allowed regulation of the maximum pressure experienced within the seamless tube, and hence the expansion of the seamless tube.

Two such experiments were conducted, both using seamless bilayer tubes. The first used bilayer tubes that expanded and contracted several percent during the pulsatile flow (and OCT imaging confirmed the corresponding smoothening of wrinkles on the inner surface of the tubes). The second used bilayer tubes whose expansion was restricted by dip-coating the outer surface with a thick sheath layer of very stiff silicone (GI-380, Silicones Inc). After 1.5 hours of circulating the platelet-rich plasma solution under pulsatile conditions, the sample and the control were both sliced open, washed gently, and fixed with formalin. They were then stained with a Wright-Giemsa stain to enable easy identification of the deposited platelets. The inner surface showed heavy platelet adhesion on the control sample whose expansion/contraction was restricted and hence had a static luminal topography. In contrast, the platelet deposition on the sample that was allowed to expand and contract (and therefore continually transition from a smooth to a wrinkled lumen) showed much lower platelet deposition.

A potential mechanism to explain the foregoing results may be based on a competition between elastic energy and adhesion energy.

It is contemplated that for a solid-like foulant to adhere onto a curved surface, it must either deform or have a reduced contact with the surface. This either poses an elastic energy penalty (if the foulant deforms along with the surface) or reduced adhesion strength (if the foulant does not deform), either of which may reduce fouling. However, the experiments found that fouling reduces considerably even at wrinkle wavelengths that are at least an order of magnitude larger than the foulant size (platelets in the present case). Thus, such an adhesion-strength-based explanation cannot operate on the level of single platelets. It could nevertheless apply to a collection of platelets, e.g. a thrombus, which can be several tens of microns in size. This adhesion-based mechanism ("the proposed mechanism") can then be summarized as follows. A patch of foulant is large enough to "feel" the changes in topography of the substrate. As the surface wrinkles, the patch seeks to deform conformally, but the change in curvature imposes an elastic energy penalty. Beyond a certain curvature, the increase in elastic energy forces delamination. A well-known mode of delamination initiates at the edge of a thin film adhering to a substrate that is stretched or compressed. Unlike the proposed mechanism, in that case, there an increase in elastic energy of both the substrate and the film, which drives a sliding mode ("Mode II") fracture at the interface. Another well-known delamination mode is of buckle delamination: a thin film attached to a substrate, upon being compressed, starts buckling at some defect location when a critical stress is reached. Once buckle delamination initiates, it can propagate into a wider buckle by peeling off the substrate. In that case, prior to buckling, the film is trying to conform to the smaller length/area of the substrate. In contrast, the proposed mechanism, to a first approximation, the contour length/surface area of the substrate remains constant; instead film is trying to conform to the bending, and hence curvature changes, of the substrate. Finally, a stiff film bonded to a soft substrate may first wrinkle under compression, and then delaminate. That situation is also different from the proposed mechanism; in the proposed mechanism, the delamination layer is presumed to be significantly softer than the substrate.

A second potential explanation is based on the kinetics of platelet attachment. All samples, even the static ones exposed to rocking contact with blood, experienced some blood flow. It is well-known that platelets spread upon attaching to a surface over a timescale of several seconds or minutes. Since the surface is constantly evolving over a timescale faster than the spreading kinetics, it is speculated that the gentle flow is adequate to constantly remove the platelets before they can attach firmly. In a more phenomenological sense, clinicians generally identify stasis (i.e. lack of blood flow) at the prime cause of thrombosis, and by increasing flow near the surface, the platelet deposition may be reduced.

Example 4

The possible mechanism of competition between elastic energy and adhesion energy was tested experimentally.

Silicone rubber surfaces were constructed that were smooth when stretched and wrinkled when retracted. They were fabricated as follows. A thin film of silicone of thickness of several ten microns of silicone rubber RTV-4136M was cast onto an acrylic sheet. A layer of much softer silicone rubber (GI-245, Silicones Inc) cast on top of this sheet. Upon curing, this yielded a stress-free bilayer. A second layer of RTV-4136M of about 2 mm thickness was cast separately. Upon curing, this latter layer was cut into a strip, about 1 inch wide and several inches long. A custom built stretching jig was used to clamp the ends of these strips and then to hold them stretched at a strain of 40%. The bilayer was then bonded onto the top surface of this pre-stretched sheet using additional uncured GI-245 silicone as a bonding material. Upon full curing, the result was a tri-layer sheet (thick RTV-4136M at the bottom, GI245 in the middle, and the thick film of RTV-4136M at the top). Upon releasing the prestretch, the top surface showed strong wrinkles of wavelength 1.7 mm. This tri-layer sheet was then clamped into a motorized stretching jig which allowed stretching and unstretching the sheet at carefully controlled rates. The tri-layer was stretched to over 40% to ensure that the wrinkles completely smoothed out.

Separately, silicone sheets of GI245 were cast in the range of thickness of 250-2750 μm in thickness. These sheets will be called the "adlayer" in this section. These were cut into strips that were roughly 1 cm×3 cm. These strips were then placed gently onto the top of the stretched and smooth tri-layer taking care to ensure full adhesion without any blisters. The prestretch was then gradually removed at a velocity of 0.05 mm/s to allow the tri-layer to retract while the entire process was video-recorded. Strain was measured by tracking the distance between markers placed every 0.5 mm in the flat/stretched configuration The retraction induced wrinkles to form, and the adlayer was observed to bend so as to follow the wrinkles. Upon further retraction however, the wrinkle amplitude increased, and the adlayer was found to debond from the wrinkles in complete accordance with the physical picture of a competition between elastic energy and adhesion energy.

Experiments included both the "thick-patch" situation (patch thickness exceeded wrinkle wavelength) or "thin-patch" situation (patch thickness was smaller than wrinkle wavelength). It was found that the strain was nearly independent of patch thickness in the thick-patch situation, whereas it increased with decreasing patch thickness in the thin-patch situation. This is in accord with the simulation results above.

With respect to technological implications of the results, first, it is found that continual topographic transition of a surface between highly wrinkled and less wrinkled states had an anti-thrombotic effect. Second is the method of driving the topographic transition. A dynamic surface must have some driving force to actuate the surface. This may be pH for materials based on hydrogels, temperature for shape-memory metals or shape-memory polymers, mechanical pressure for pneumatic actuation, or light for liquid crystal elastomers. In the cardiovascular system, the natural cardiac cycle and pulse pressure can drive topographic changes in vascular grafts. This has the potential to allow practical implementation in grafts without external power. Third, the effects seem to be independent of surface chemistry. Accordingly, these "mechanical" effects may be used synergistically with any chemical modification of the surface. Finally, the mechanism of anti-fouling action inducted by topographic may be general and therefore, useful for other types of fouling, e.g. bacterial biofouling or mineral deposition.

We claim:

1. A method of actuating an anti-fouling surface of a vascular implant device to continually cycle between a smooth base topography and a deformed topography, and reverse to a smooth base top, comprising:
   forming a vascular implant composite, comprising:
      selecting a first layer composed of a first material having a surface topography and a first modulus;
      providing an initial smooth base surface topography to the first layer;
      selecting a second layer composed of a second material having a different second modulus,
   wherein a ratio of the first modulus to the second modulus is from about 3:1 to about 10,000,000:1; and
      connecting the second layer to the first layer;
   cycling the surface topography of the first layer, comprising:
      applying a mechanical strain to the vascular implant composite, comprising:
         repeatedly actuating one or more wrinkles or folds to form one or more reversible deformed surface topographies on the first layer,
   wherein the repeatedly actuating step is provided by continual variation of blood pressure between systol and diastole, and
   wherein the surface topography of the first layer continually transitions between a smooth surface topography and one or more reversible deformed surface topographies as a result of the continual variation of blood pressure between systol and diastole in a natural circulatory system of a body.

2. The method of claim 1, wherein the cycling the surface topography of the first layer is structured to reduce or prevent thrombus formation when in contact with blood.

3. The method of claim 1, wherein the cycling the surface topography of the first layer is structured to control platelet adhesion when in contact with blood.

4. The method of claim 1, wherein the cycling the surface topography of the first layer further comprises producing instability of the topography, and controlling wavelength of the topography.

5. The method of claim 1, further comprising the step of reversing from the one or more reversible deformed surface topographies to the initial smooth base surface topography.

* * * * *